(12) United States Patent
Flemmig et al.

(10) Patent No.: US 6,648,644 B1
(45) Date of Patent: Nov. 18, 2003

(54) SUBGINGIVAL TREATMENT BY POWDER JET

(75) Inventors: Thomas Flemmig, Muenster (DE); Bernd Gangnus, Andechs (DE); Oswald Gasser, Seefeld (DE); Rainer Guggenberger, Herrsching (DE)

(73) Assignee: ESPE Dental AG, Seefeld (DE)

( * ) Notice: Subject to any disclaimer, the term of this patent is extended or adjusted under 35 U.S.C. 154(b) by 0 days.

(21) Appl. No.: 09/936,163

(22) PCT Filed: Mar. 9, 2000

(86) PCT No.: PCT/EP00/02039

§ 371 (c)(1),
(2), (4) Date: Oct. 18, 2001

(87) PCT Pub. No.: WO00/53154

PCT Pub. Date: Sep. 14, 2000

(30) Foreign Application Priority Data

Mar. 10, 1999 (DE) .......................................... 199 10 559

(51) Int. Cl.⁷ ............................. A61C 15/00; A61C 3/02
(52) U.S. Cl. .......................................... 433/216; 433/88
(58) Field of Search ........................... 433/88, 215, 216

(56) References Cited

U.S. PATENT DOCUMENTS

| 4,214,871 | A | * | 7/1980 | Arnold ........................ 433/216 |
| 5,203,698 | A | * | 4/1993 | Blake et al. ................. 433/216 |
| 5,865,620 | A | * | 2/1999 | Kutsch ........................ 433/88 |
| 6,342,207 | B1 | * | 1/2002 | Stoor et al. ................... 424/49 |

FOREIGN PATENT DOCUMENTS

| DE | 2930836 | 2/1980 |
| GB | 988513 | 4/1965 |
| GB | 1480594 | 7/1977 |

OTHER PUBLICATIONS

Patent Abstract of Japan: vol. 016, No. 081, Feb. 27, 1992 & JP 03 271215 A (KAO), Dec. 3, 1991 Zusammenfassung.

* cited by examiner

Primary Examiner—Cary E. O'Connor
(74) Attorney, Agent, or Firm—Birch, Stewart, Kolasch & Birch, LLP

(57) ABSTRACT

The invention relates to the use of fine powders or powder mixtures for the preparation of an agent for powder-jet cleansing of dental root surfaces, wherein the powders or powder mixtures provide a density of no more than 2.0 g/cm³ and/or a mean particle size of no more than 45 µm.

9 Claims, No Drawings

SUBGINGIVAL TREATMENT BY POWDER JET

This application is the national phase under 35 U.S.C. §371 of PCT International Application No. PCT/EP00/02039, which has an International filing date of Mar. 9, 2000, which designated the United States of America and was not published in English.

The present invention relates to the use of fine powders in a process for cleansing dental root surfaces.

One in every five to seven adults suffers from marginal periodontitis. Periodontal diseases are caused by the accumulation of bacteria on the tooth where they form a bioflim referred to as a bacterial plaque and further colonise the gum pockets. The disease is characterised by inflammation of the periodontal soft tissue, exposure of the root surface, formation of periodontal pockets and progressive degradation of the tooth-bearing, fibrous structure and alveolar bone. If untreated, marginal periodontitis often leads to tooth loss. Tartar, which is formed by the mineralisation of the dead bacterial plaque, is not in itself pathogenic. However, it is generally covered with a living bacterial plaque.

One essential goal of periodontitis therapy is to prevent the progressive destruction of the tooth-bearing structure and thereby to avoid the loss of teeth through periodontal disease. To this end, the bacterial plaque and tartar are removed above (supragingivally) and, where accessible, also below the edge of the gum (subgingivally). In the case of progressive periodontal disease, periodontal surgery is often additionally required in order to achieve complete cleansing of the subgingival areas of the root. This treatment only leads to a short-term healing of the periodontal tissue. Even with adequate oral hygiene, an almost complete bacterial re-colonisation of the periodontal pocket can occur within a few months (Haffajee et al. 1997, J Clin Periodontol 24:324–334), and consequently, the newly formed plaque must be professionally removed at three to six-month intervals in order to maintain the health of the marginal periodontium (Axelsson and Lindhe 1981, J Clin Periodontol 8:281–294). This supporting periodontal therapy uses primarily curettes, sonic and ultrasonic de-scaling instruments. The use of these instruments requires technical skill on the part of the treating operator and is generally felt by patients to be unpleasant. Repeated cleansing in the context of supporting periodontal therapy leads cumulatively to a clinically relevant removal of root material which can cause hypersensitivity and weakening of the root or even perforation of the root canal system and a risk of fracture (Zappa et al. 1991, J Periodontol 62:750–754, Flemmig et al. 1998, J Periodontol 69:547–533).

Supragingival tooth surfaces can be cleansed very efficiently with a powder-air-water (PAW) jet (U.S. Pat. No. 4,595,365). With regard to its abrasiveness in cleansing the tooth enamel, the jet spraying agent previously used in PAW devices (sodium hydrogen carbonate) is not critical, however, when used on the root, it can quickly lead to a clinically relevant abrasion of material (Boyde 1984. Brit Dent J 156:287–29 1). Since the root is exposed in cases of marginal periodontitis, the PAW jet using the conventional agent is of limited usefulness for supporting therapy of periodontitis.

GB 1 480 594 discloses a process for tooth cleansing using a water jet. The water jet contains particles of a hardness which avoids the destruction of the tooth enamel. Calcium lactate, crystalline fruit acids, dextrins, gelatins, crystalline weak acids, mineral salts and bone glue are named as examples. The disadvantage of this process is that the substances disclosed are not, in every case, suitable for cleansing subgingival tooth enamel.

The object of the present invention is therefore to provide simple and gentle agents and methods for cleaning root surfaces, i.e. subgingival tooth enamel.

This object is resolved by the preparation and use of powders or powder mixtures according to the patent claims.

These powders preferably provide an abrasiveness which achieves an abrasion of root dentine of at least 50% less than powders or powder mixtures based, for example, on sodium hydrogen carbonate of mean particle size approx. 55 $\mu$m, which are conventionally used for cleansing supragingival tooth surfaces.

Surprisingly, it was found that the powders or powder mixtures which fulfil these conditions are outstandingly suitable for cleansing root dentine, without abrading noticeable quantities of healthy root substance.

The treatment operator uses the powders or powder mixtures by directing the powder jet towards the position to be cleansed and implementing the cleansing by briefly applying the jet to the surface of the root dentine. Since, in this process, the powder jet also penetrates a few mm deep into the periodontal pocket, it is often not necessary to open the gum surgically before cleansing, as in the case of the conventional process. This represents a considerable saving in time for the person carrying out the treatment; for the patients it also means a significant reduction in stress, because not even a local anaesthetic is required.

The invention will be elucidated in greater detail below.

Powders or powder mixtures which are suitable for use according to the invention are such that they can be pumped by means of conventional powder-jet devices used in dentistry.

The powders or powder mixtures provide a mean particle size of no more than 45 $\mu$m. The particle size of the powders or powder mixtures is preferably within a range from 0.01 $\mu$m to 45 $\mu$m. The preferred particle size is within the range from 0.05 $\mu$m to 45 $\mu$m, especially from 0.1 to 45 $\mu$m. The mean particle size is preferably less than 35 $\mu$m.

The density of the powders or powder mixtures is no more than 2.0 g/cm$^3$.

One decisive criterion for the usefulness of the powders or powder mixtures is their abrasiveness in respect of root dentine, i.e. subgingival tooth enamel. The time required for cleansing one root surface in the context of a periodontal treatment using the powders or powder mixtures disclosed here is approximately one minute. This means that within this time, no substantial abrasion of the root dentine should occur.

A test was therefore developed for the selection of suitable powders or powder mixtures, according to which the abrasiveness of jet agents in respect of root dentine can be measured under laboratory conditions. The abrasiveness of the said powders or powder mixtures is measured in this context in such a manner that a bovine root-dentine surface of 9.6 mm$^2$ is sprayed for 1 minute with a pumping pressure of 4.0 bar from a distance of 2.3 mm. The treated surfaced is then measured microscopically and the volume of bovine dentine abraded is calculated from these measured data. The commercially available powders normally used for cleansing tooth enamel (e.g. Air-Flow-Powder, manufactured by EMS) provide an abrasion in this test of approximately 1.24 mm$^3$. This is also optically identifiable and clinically unacceptable.

Surprisingly, it was found that certain powders or powder mixtures provide an abrasiveness in the process described above which significantly lower, but still high enough to remove undesired coatings from the root dentine, and therefore allow an efficient powder-jet cleansing of root surfaces.

Powders suitable for cleansing root surfaces included for example, amino acids, sugars, organic acids and their salts, especially glycine, urea, potassium hydrogen phthalate or potassium-D-gluconate. In this context the powders used preferably provide a particle-size distribution from 0.05 preferably from 0.1 μm to 45 μm.

Of course, powder mixtures of at least two powders are also suitable for the purpose described. The mixing ratio in this context may be selected freely, but when using two powders is preferably within the range from 1:10 to 10:1 relative to the mass of the powders to be mixed.

All of the powders named as examples share the characteristic that they normally provide a lower density than powders or powder mixtures used hitherto for supragingival tooth cleansing.

Experiments have shown the surprising result that these powders already used for supragingival application are only suitable for cleansing root surfaces if they are ground significantly more finely and therefore provide a lower mean particle size.

It may be advantageous to mix the previously named powders with other, very fine powders before they are used as cleansing agents for root surfaces. This may have the effect that the resulting powder mixtures can be pumped better and faster using conventional powder-jet devices.

Highly dispersed silicic acids or aerosils, preferably with an average particle size of approximately 0.07 μm may be named as examples of such very fine powders. The amount to be added is preferably within the range from 0.001 to 5.0% by weight, especially within the range from 0.01 to 0.1% by weight relative to the total mass of powder.

The addition of other finely ground substances, for example, bleaching agents such as perborates (e.g. sodium perborate), fluoride-releasing substances, such as sodium fluoride, analgesics such as articain or lidocain, bactericides such as chlorhexidine or triclosan, flavourings such as citric acid and/or ascorbic acid is also a possibility. The quantity to be added is preferably within the range from 0.001 to 5.0% by weight, especially within the range from 0.01 to 0.1% by weight relative to the total mass of the powder.

The area of application of the powder described may be expanded depending on the substance added. For example, the use of flavouring agents may increase patient acceptance.

The powders may, if required, also be provided with a surface coating. Appropriate surface coating agents may be named as: starch, alginates, collagen (gelatins), hydrogels, polyanhydrides, polyester, poly imino carbonates, polycaprolactones, poly amino acids, polyphosphazenes. The use of microencapsulation techniques has proved advantageous in this context.

Moreover, the surface structure can also be influenced via controlled crystallisation, in order to achieve the desired abrasiveness. The crystallisation forms: monoclinic, rhomboidal prismatic, tetragonal-scaleneohedral and orthorhombic have proved favourable.

Preparation of Bovine Tooth Roots and Implementation of Measurements

For each experiment, 3 freshly extracted bovine teeth were used; after cleaning by rinsing with deionised water, the surface of the root area was smoothed by treatment with an abrasive paper. The bovine tooth roots prepared in this manner were fixed in an embedding compound (Reprogum®, manufactured by Espe, Seefeld) and covered with a plastic plate providing a circular opening of 3.5 mm diameter. The exposed dentine surface of the bovine tooth was then sprayed for one minute using a powder-spraying device (Airflow®, manufactured by EMS, Munich) with the corresponding powder or powder mixture at a jet pressure of 4.0 bar and a distance between root surface and jet nozzle of 2.3 mm. For every experiment, the powder tanks were filled to the maximum.

To measure the volume of abraded bovine-root dentine, a cast of the sprayed surfaces was made using a moulding compound (Dimension Garant®, manufactured by Espe, Seefeld). The resulting negative of the volume abraded, in the form of a semi-ellipsoid, was measured along its axes using a light microscope. The volume abraded was calculated on the basis of these data with the assistance of the following formula:

$$\text{Volume abraded} = \tfrac{2}{3}\pi a \cdot b \cdot c$$

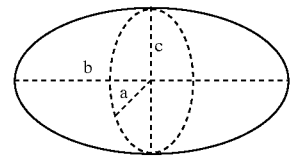

FIG. 1: Diagram of the semi-ellipsoid for calculation of the abraded volume.

EXAMPLE I

Preparation of a Powder Mixture I According to the Invention 100 g glycine (manufactured by Fluka, Deisenhofen) were ground for 3 minutes in an agate disc grinder and then sieved dry over a 40 μm sieve. Then 0.36 g HDK-H-2000 (manufactured by Degussa, Hanau) were added to the powder obtained in this manner, and this mixture was sieved again over a 60 μm sieve.

EXAMPLE II

Preparation of a Powder Mixture II According to the Invention 100 g potassium-D-gluconate (manufactured by Fluka, Deisenhofen) were ground for 4 minutes in an agate disc grinder and then sieved dry over a 40 μm sieve. Then 0.63 g HDK-H-2000 (manufactured by Degussa, Hanau) were added to the powder obtained in this manner, and this mixture was sieved again over a 60 μm sieve.

EXAMPLE III

Preparation of a Powder Mixture III According to the Invention 100 g potassium hydrogen phthalate (manufactured by Fluka, Deisenhofen) were ground for 3 minutes in an agate disc grinder and then sieved dry over a 40 μm sieve. Then 0.79 g HDK-H-2000 (manufactured by Degussa, Hanau) were added to the powder obtained in this manner, and this mixture was sieved again over a 60 μM sieve.

EXAMPLE IV

Preparation of a Powder Mixture IV According to the Invention 100 g urea (manufactured by Fluka, Deisenhofen) were ground for 2 minutes in an agate disc grinder and then sieved dry over a 40 μm sieve. Then 0.18 g HDK-H-2000 (manufactured by Degussa, Hanau) were added to the powder obtained in this manner, and this mixture was sieved again over a 60 μm sieve.

EXAMPLE V

Preparation of a Powder Mixture V According to the Invention 100 g sodium hydrogen carbonate (manufactured by Fluka, Deisenhofen) were ground for 2.5 minutes in an agate disc grinder and then sieved dry over a 40 μm sieve. Then 0.19 g HDK-H-2000 (manufactured by Deeussa, Hanau) were added to the powder obtained in this manner and this mixture was sieved again over a 60 μm sieve.

EXAMPLE VI
Preparation of a Powder Mixture VI According to the Invention 100 g sodium ascorbate (manufactured by Fluka, Deisenhofen) were ground for 1 minute in an agate disc grinder and then sieved dry over a 40 μm sieve. Then 0.9 g HDK-H-2000 (manufactured by Degussa, Hanau) were added to the powder obtained in this manner, and this mixture was sieved again over a 60 μm sieve.

EXAMPLE VII
Preparation of a Powder Mixture VII According to the Invention 100 g Air-Flow-Powder (manufactured by EMS) were ground for 1 minute in an agate disc grinder and then sieved dry over a 40 μm sieve. Then 0.9 g HDK-H-2000 (manufactured by Degussa, Hanau) were added to the powder obtained in this manner, and this mixture was sieved again over a 60 μm sieve.

Control Example: Not According to the Invention 100 g Air-Flow-Powder (manufactured by EMS) were used as supplied by the manufacturer.

The powder mixtures I–VII were placed into the powder-jet device (Airflow®, manufactured by EMS, Munich) and used as described above. The quantity of bovine root dentine abraded in each case is shown in Table 1.

TABLE 1

Volume of bovine root dentine abraded in dependence upon the powder mixture used or its density and mean particle size.

| Powder mixture | Density [g/cm$^3$]* | Mean particle size [μm]** | Volume abraded [mm$^3$] |
|---|---|---|---|
| I | 1.16 | 10.7 | 0.07 |
| II | 1.73 | 21.7 | 0.043 |
| III | 1.64 | 10.7 | 0.062 |
| IV | 1.34 | Approx. 12 (estimated) | 0.022 |
| V | 2.16 | 35.9 | 0.441 |
| VI | 1.80 | 21.0 | 0.206 |
| VII | 2.16 | 34.8 | 0.440 |
| Control | 2.16 | 54.3 | 1.24 |

*Source: Beilstein
**Measured using granulometers manufactured by CILAS with isopropanol as dispersal agent.

The density of the powders used corresponds to the values indicated in standard reference books and is dependent on the relevant crystal structure. The particle-size distribution and the mean particle size can be determined using methods such as sieves or granulometers (e.g. manufactured by Silas) which are familiar to a person skilled in the art.

What is claimed is:

1. A method for cleansing teeth, which comprises applying to subgingival tooth enamel a fine powder or powder mixture in the form of a powder-jet cleansing agent, wherein the powder or powder mixture particles have a mean particle size of no more than 45 μm and a density of no more than 2.0 g/cm$^3$.

2. The method according to claim 1, wherein the powder or powder mixture comprises at least two finely particulate substances.

3. The method according to claim 2, wherein one of the finely particulate substances is selected from the group consisting of silica gel, bleaching agents, analgesics, bactericides and/or flavourings.

4. The method according to claim 1, wherein the fine powder or powder mixture comprises particles formed from a member selected from the group consisting of amino acids, sugars, organic acids, organic acid salts, sugars and organic acids, and sugars and organic acid salts.

5. The method according to claim 4, wherein the organic acid salts are alkaline, earth alkaline or ammonium salts.

6. The method according to claim 1, wherein the powder or powder mixtures are expelled by means of a pressurized jet device.

7. The method according to claim 1, wherein the powder or powder mixtures comprises at least two types of finely particulate substances, the first type being selected from silica gel, bleaching agents, analgesics, bactericides and/or flavourings; and the second type being selected from the group consisting of amino acids, sugars, organic acids, sugars and organic acids, and sugars and organic acid salts.

8. The method according to claim 7, wherein the organic acid salts are alkaline, earth alkaline or ammonium salts.

9. The method according to claim 1, wherein the mean particle size is no more than 35 μm.

* * * * *

UNITED STATES PATENT AND TRADEMARK OFFICE
CERTIFICATE OF CORRECTION

PATENT NO.   : 6,648,644 B1
DATED        : November 18, 2003
INVENTOR(S)  : Flemmig, Thomas It is certified that error appears in the above-identified patent and that said Letters Patent is hereby corrected as shown below:

Column 1,
Line 3, delete "Bioflim" and insert -- Biofilm --.
Line 57, delete "1984." and insert -- 1984, --.

Column 3,
Line 57, after "measurements" insert -- : --.

Column 4,
Line 65, delete "Deeussa" and insert -- Degussa --.

Column 5,
Line 21, delete "Plow" and insert -- Flow --.

Signed and Sealed this

Tenth Day of January, 2006

JON W. DUDAS
*Director of the United States Patent and Trademark Office*